(12) United States Patent
Bunn et al.

(10) Patent No.: US 7,988,647 B2
(45) Date of Patent: Aug. 2, 2011

(54) ASSESSMENT OF MEDICAL CONDITIONS BY DETERMINING MOBILITY

(76) Inventors: Frank E. Bunn, Thornhill (CA);
Richard D. Adair, Waterloo (CA);
William R. Bauer, Port Clinton, OH (US)

(*) Notice: Subject to any disclaimer, the term of this patent is extended or adjusted under 35 U.S.C. 154(b) by 23 days.

(21) Appl. No.: 12/382,401

(22) Filed: Mar. 16, 2009

(65) Prior Publication Data
US 2010/0049095 A1   Feb. 25, 2010

Related U.S. Application Data

(60) Provisional application No. 61/036,492, filed on Mar. 14, 2008.

(51) Int. Cl.
*A61B 5/103* (2006.01)
*A61B 5/117* (2006.01)

(52) U.S. Cl. ........................ 600/595; 600/587

(58) Field of Classification Search ............. 600/300, 600/301, 587–595; 702/127, 138–154
See application file for complete search history.

(56) References Cited

U.S. PATENT DOCUMENTS

| | | |
|---|---|---|
| 4,813,436 A | 3/1989 | Au |
| 5,511,571 A | 4/1996 | Adrezin |
| 5,623,944 A | 4/1997 | Nashner |
| 5,807,283 A | 9/1998 | Ng |
| 5,831,937 A | 11/1998 | Weir |
| 5,919,149 A | 7/1999 | Allum |
| 6,010,465 A | 1/2000 | Nashner |
| 6,231,527 B1 | 5/2001 | Sol |
| 6,360,597 B1 | 3/2002 | Hubbard, Jr. |
| 6,584,403 B2* | 6/2003 | Bunn ............. 701/213 |
| 7,141,026 B2 | 11/2006 | Aminian |
| 7,172,563 B2 | 2/2007 | Takiguchi |
| 7,191,644 B2 | 3/2007 | Haselhurst |
| 7,244,231 B2 | 7/2007 | Dewing |
| 2006/0028556 A1* | 2/2006 | Bunn et al. ....... 348/211.99 |
| 2006/0190419 A1* | 8/2006 | Bunn et al. ............ 706/2 |

FOREIGN PATENT DOCUMENTS

WO   WO2005001768   1/2005

OTHER PUBLICATIONS

Scott, Vicky et al. Multifactorial and Functional Mobility Assessment Tools for Fall Risk Among Older Adults in Cummunity, Home-Support, Long-Term and Acute Care Settings. The Journal of Age and Ageing (2007); 36: 130-139. Feb. 10, 2007. Oxford University Press.

* cited by examiner

*Primary Examiner* — Jeffrey G Hoekstra

(57) ABSTRACT

A mobility assessment detects abnormalities in motion using a stagger algorithm. The detected abnormalities are compared to known norms for a particular test to determine if the abnormalities are normal or not. The comparison can be made for abnormalities associated with different diseases and illnesses to classify whether or not the condition exists and its phase. The results may be used to generate a treatment regime.

13 Claims, 14 Drawing Sheets

Figure 1 Sit - Stand Assessment of a Subject

Detection of Movement Deviation from "Normal" or "Standard"
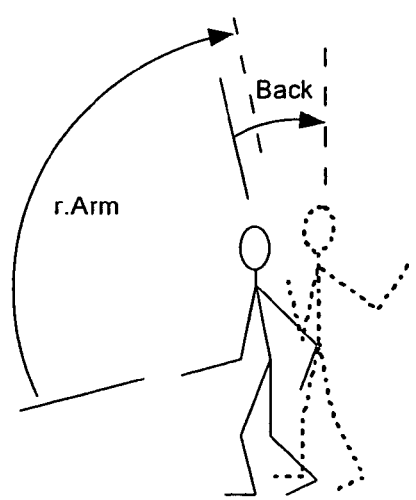
Step forward results in stagger backward
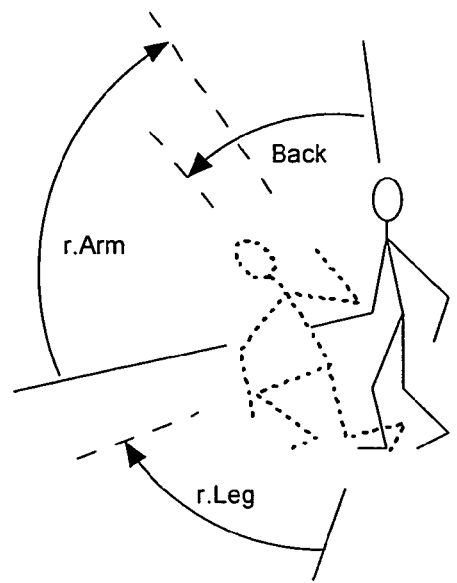
Step forward results in stagger forward
Figure 4  Stagger Movements

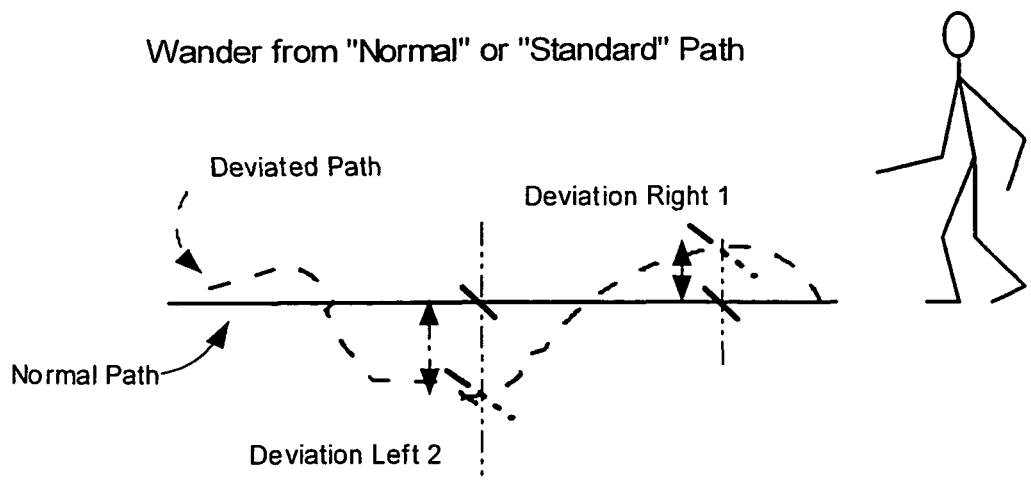
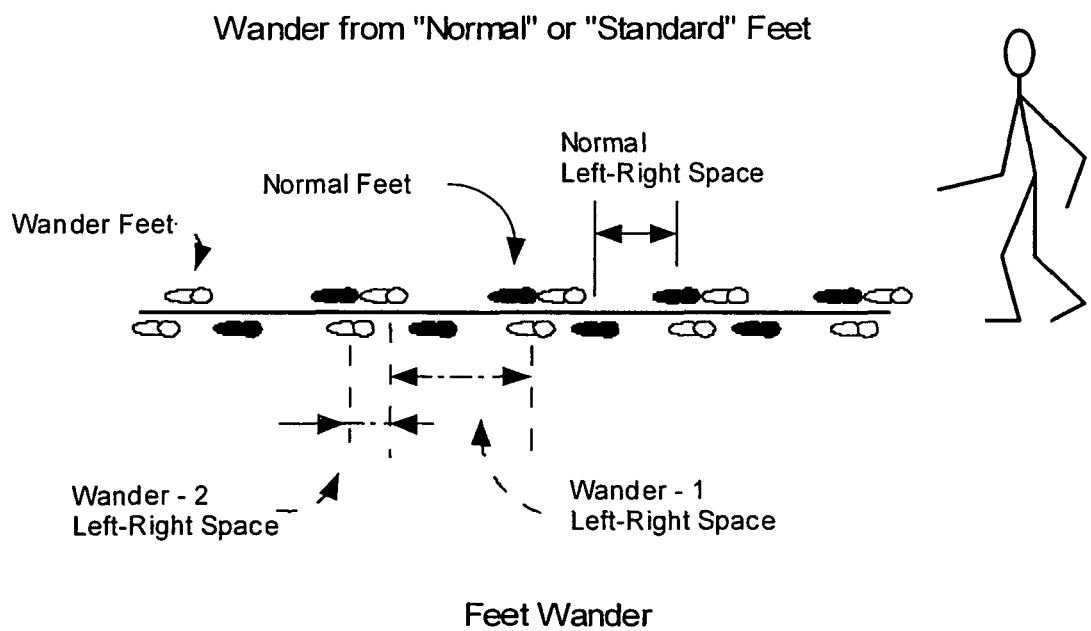
Figure 5  Wander From Path, Step Size Wander

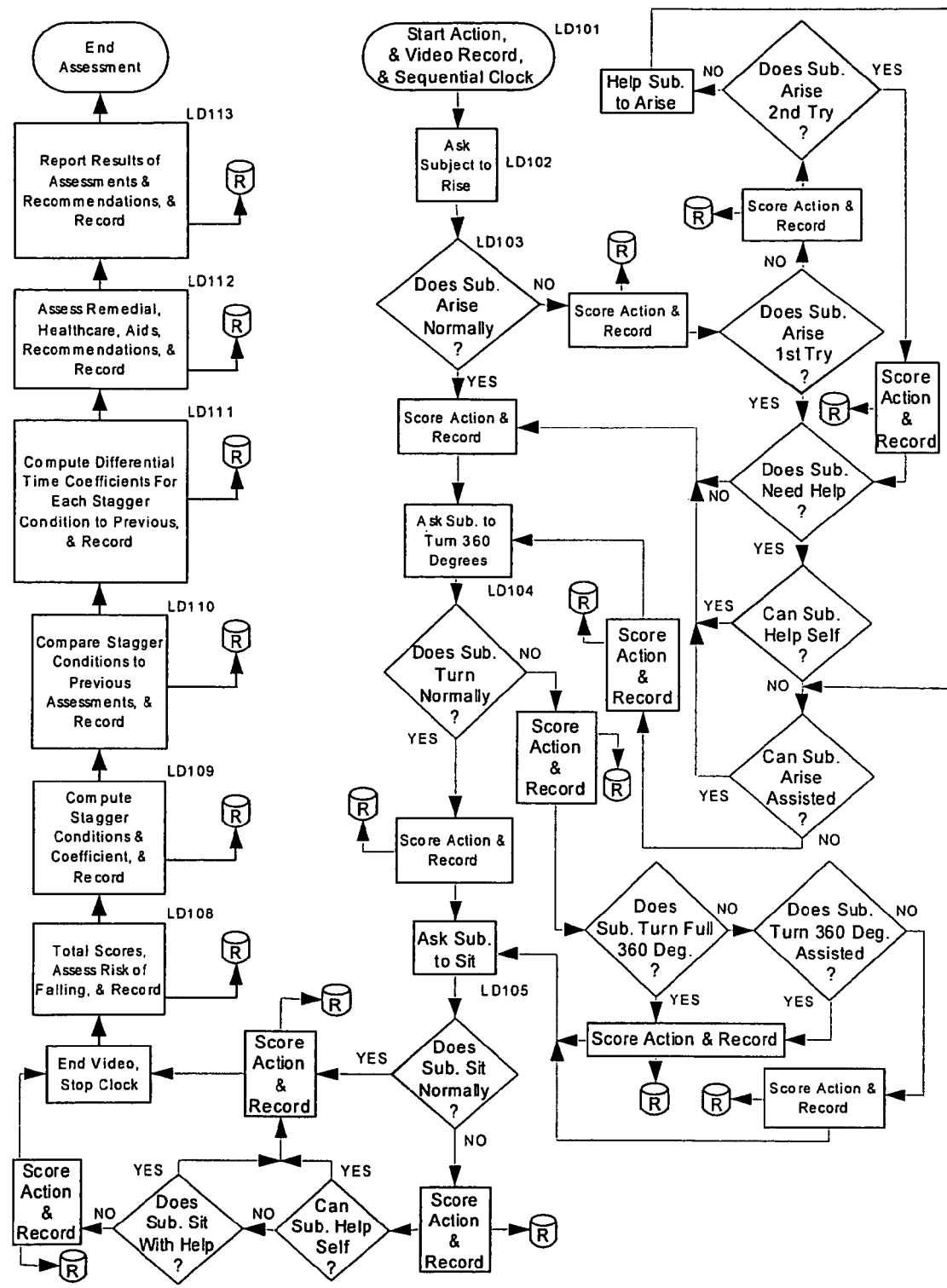
Figure 7  Logic Diagram 1: Sit - Stand - Turn - Sit Mobility

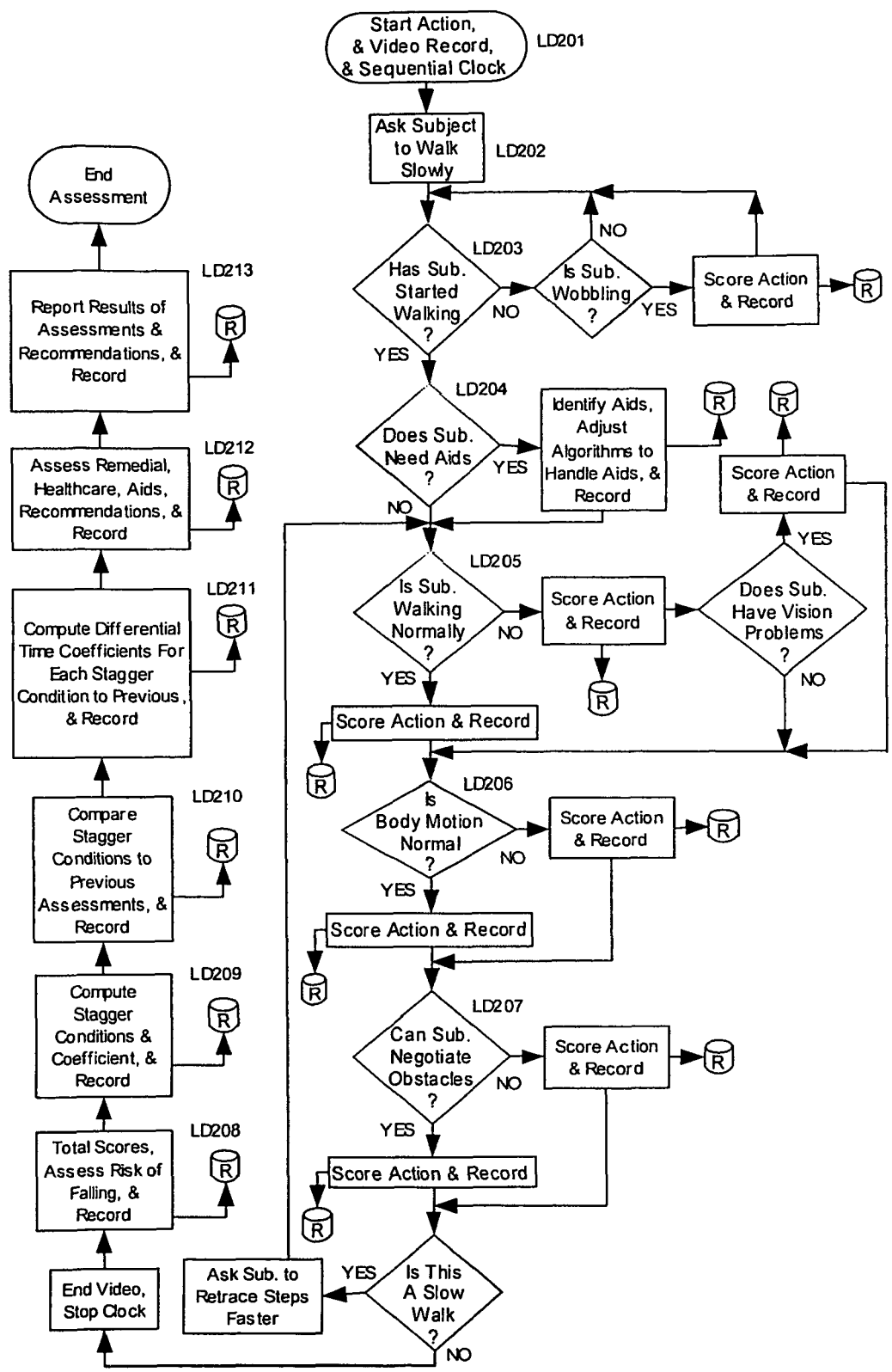
Figure 8  Logic Diagram 2: Walk Slow - Negotiate - Walk Fast Mobility

Equation 1

Stagger Condition = S   and   Time = t where $S = \dfrac{\text{distance}}{t} + \dfrac{\text{\# of steps}}{t} + \dfrac{\text{wobble degrees}}{t} + \dfrac{\text{wander}}{t} + \dfrac{\text{360 turn}}{t}$

Equation 2

Stagger Coefficient = $\triangle S$ where $\triangle S = \triangle\left(\dfrac{\text{distance}}{t}\right) + \triangle\left(\dfrac{\text{\# of steps}}{t}\right) + \triangle\left(\dfrac{\text{wobble degrees}}{t}\right) + \triangle\left(\dfrac{\text{wander}}{t}\right) + \triangle\left(\dfrac{\text{360 turn}}{t}\right)$ Figure 9   Equations for Stagger Condition & Stagger Coefficient

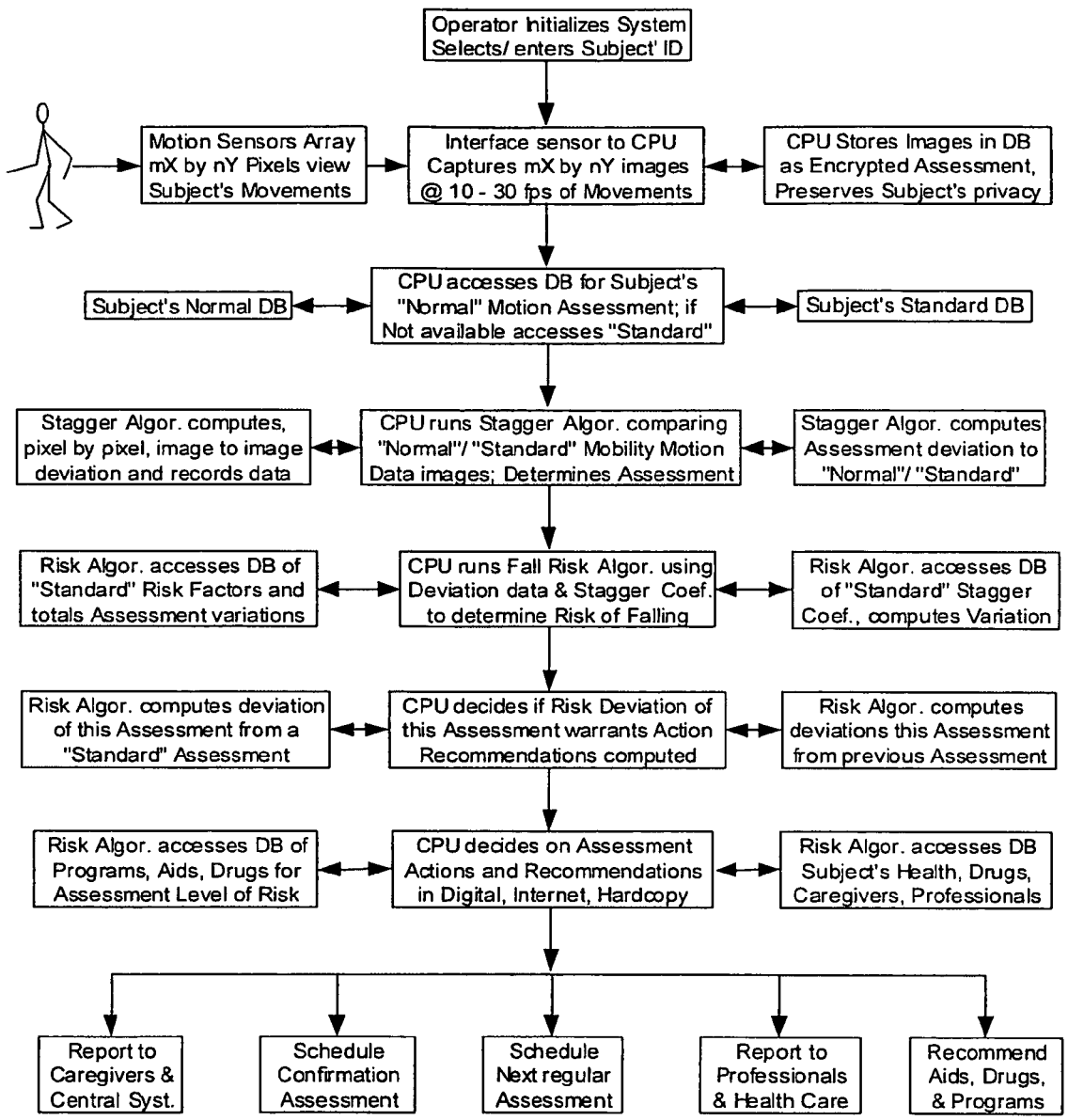
Figure 10   Computer Decision Architecture

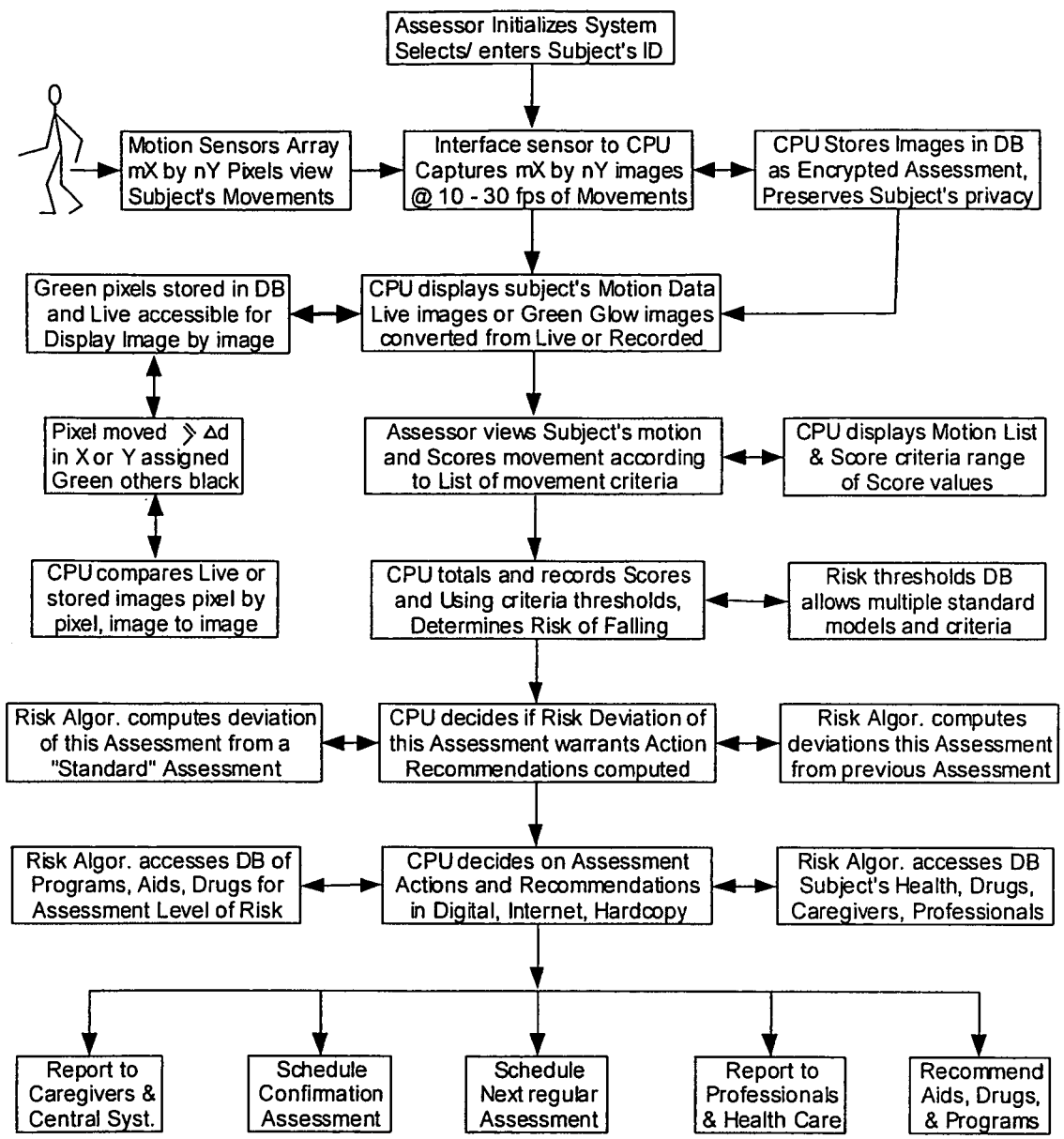
Figure 11  Assessor Decision Architecture

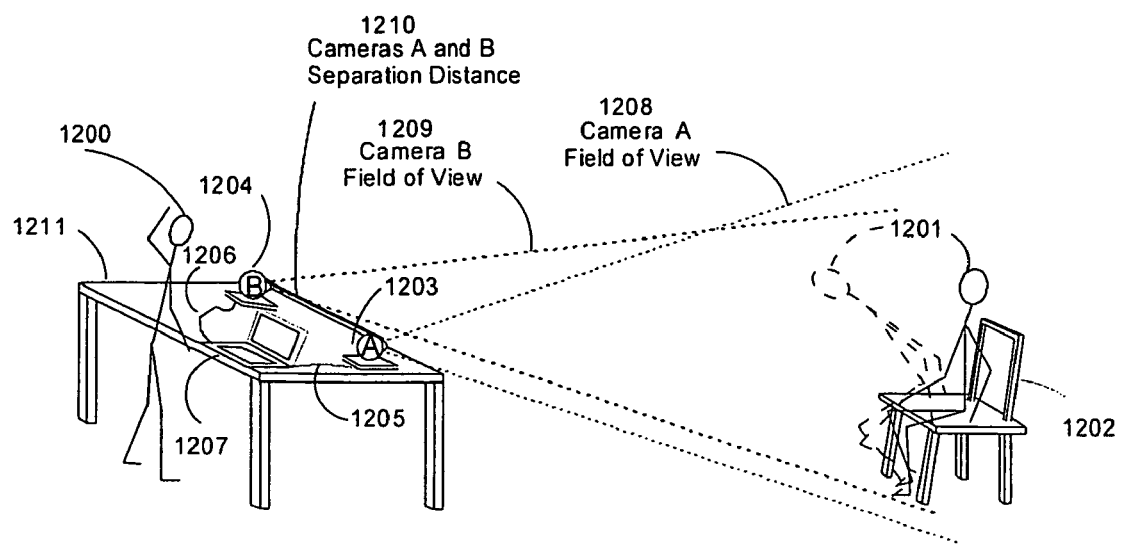
Figure 12 Sit - Stand Assessment of a Subject with 3-D Sterioscopic Cameras

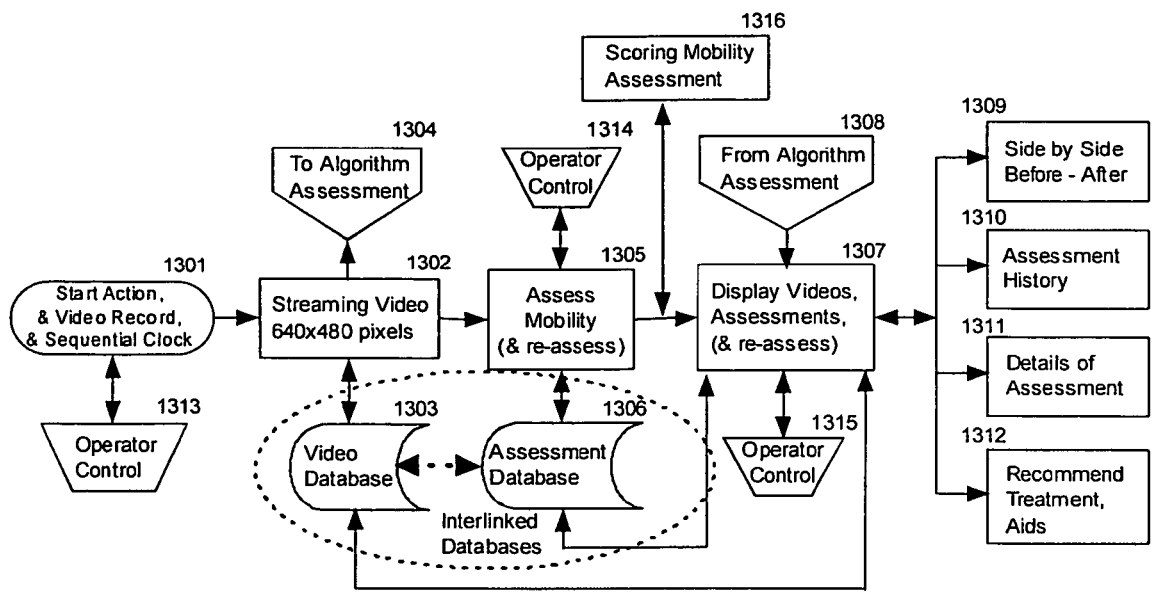
Figure 13 Logic for Basic Assessment and Display of subject mobility

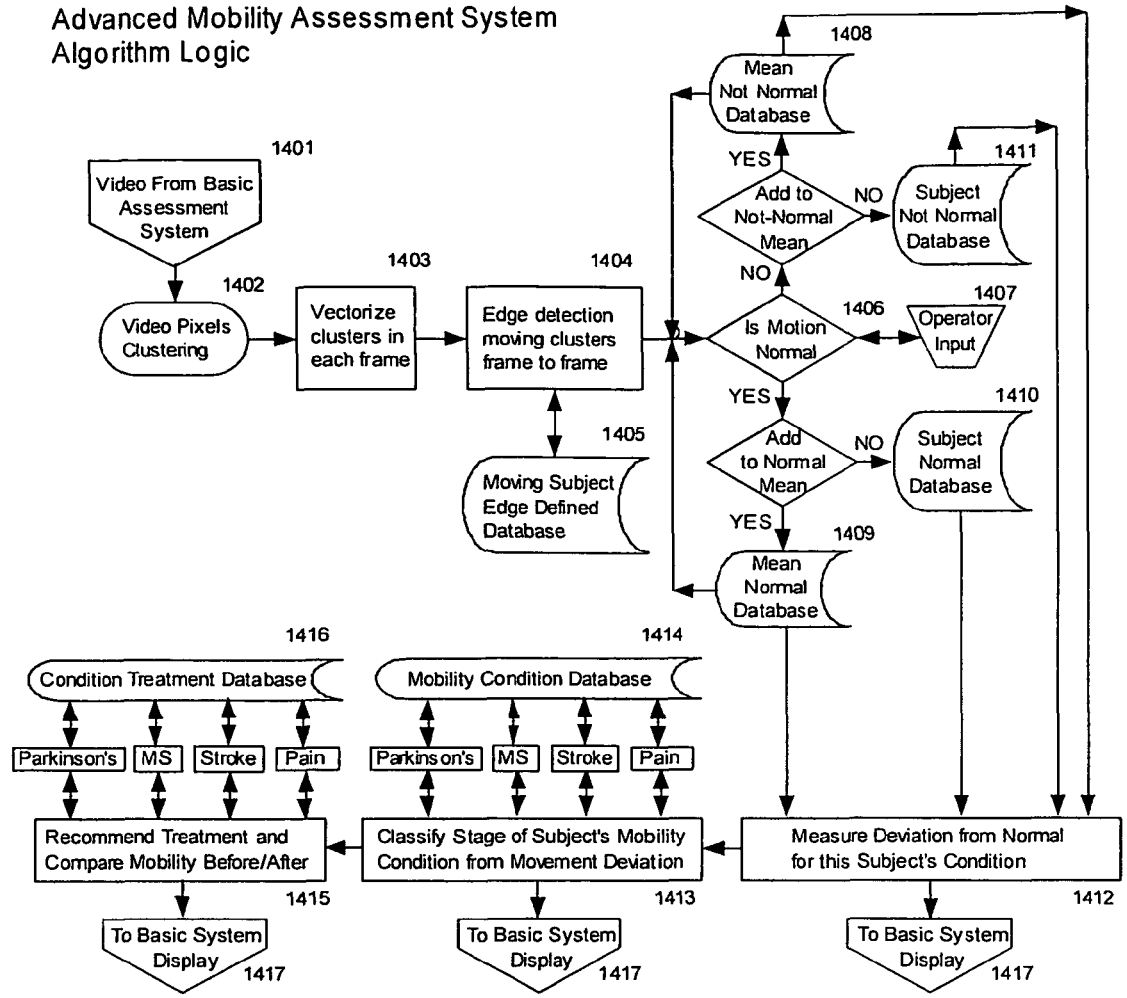
Figure 14 Logic for Training, Algorithms, and Recognition of Subject's Condition

ASSESSMENT OF MEDICAL CONDITIONS BY DETERMINING MOBILITY

This application claims priority from U.S. Application No. 61/036,492 filed on Mar. 14, 2008, the contents of which are incorporated herein by reference.

FIELD OF THE INVENTION

The present invention relates to systems and methods of assessing mobility.

BACKGROUND OF THE INVENTION

It is recognised in the medical community that assessment of the movement of a subject, generally referred to as mobility, may be us as an indicator of medical conditions, and a lack of mobility carries an attendant risk of falling. It is also well known that the population of the world is ageing, and for people over the age of 65 falling is one of the serious problems, which causes injury, reduced quality of life and often death in seniors. The medical costs to the senior, the senior's family, and to public and private health care systems from these falls is devastating. Assessing the mobility and thereby the risk of falling is a significant tool for the prevention of falls and for the determination of the implementation of procedures, practices, and aids to improve mobility, activity and a better quality of life for the ageing seniors.

Vicky Scott, British Columbia Injury Research & Prevention Unit, Ministry of Health, Office for Injury Prevention, Victoria BC, Canada, et al., in 2008 published results of an exhaustive review of published studies that test the validity and reliability of fall-risk assessment tools, titled "Multifactorial and functional mobility assessment tools for fall risk among older adults in community, home-support, long-term and acute-care settings". The results indicated some 38 such different tools were considered, all of which show moderate to good validity and reliability. However, an ongoing study by Gabriele Meyer, University of Hamburg, Unit of Health Science and Education, Hamburg, Germany, et al., in 2005 to evaluate the clinical efficacy and consequences of different fall risk assessment strategies with 54 nursing home clusters, including 1080 residents, states that only three tools have been repeatedly evaluated in geriatric populations: the Tinetti Test, the Mobility Interaction Fall Chart and the Downton Index.

Many patents have taught methods and instrumented apparatuses related to measuring parameters for mobility, stability and walking, and devising systems to aid, correct and rehabilitate movement of subjects as related to their risk of falling. Nashner, in 1997 U.S. Pat. No. 5,623,944 and again in 2000 U.S. Pat. No. 6,010,465, teaches the use of mechanical treadmills instrumented with sensors connected to computers to measure a subject's walking gait. Sol, in 2001 U.S. Pat. No. 6,231,527, teaches the use of mechanical treadmills instrumented with sensors, plus the addition of several video cameras and mirrors, producing data related to weight-bearing forces on a subject's feet while walking in instrumented shoes as a method for analyzing walking difficulties and determining orthotic solutions. Adrezin, in 1996 U.S. Pat. No. 5,511,571, teaches using mechanical walking aids such as walkers, canes or crutches wherein the actual aids are themselves instrumented with sensors to measure force loads in those aids from which to measure the gait of a walking subject.

Many patents have taught methods and instrumented subjects related to measuring parameters for a subject's body mobility, stability and walking, and devising systems to aid, correct and rehabilitate movement of those subjects as related to their risk of falling. Ng, in 1998 U.S. Pat. No. 5,807,283, teaches use of a magnetic sensor strapped to the leg of a subject, plus additional instrumentation strapped to the subject's other leg or to a specialized shoe worn by the subject, from which data are transmitted to receiving and analysis systems to measure the speed and gait of the subject. Weir, in 1998 U.S. Pat. No. 5,831,937, teaches the use of a transponder worn about the middle of the subject's centre of mass, which transmits infrared and ultrasound pulses to receiver and computer systems, from which data gait, speed, cadence, step time and step length are determined for assessment of gait pathologies. Allum, in 1999 U.S. Pat. No. 5,919,149, teaches use of angular velocity transducers attached to the upper body of a subject, to detect the movement not of a subject's feet but of the subject's body swaying in angular position and velocity, plus specialized eyewear, from which data an operator may interpret balance or gait disorders. Amimian, in 2006 U.S. Pat. No. 7,141,026, teaches a similar body movement method as does Allum, but in particular uses a gyroscope sensor attached to the trunk of a subject for the measurement of the postural transitional speed and direction of the movement from which an operator can determine the time duration of postural transitions for actions like standing and rising from sitting, related to risk of falling.

Many patents have taught methods and instrumented subjects related to measuring parameters of a subject's feet movement relating to the subject's walking gait. Takiguchi, in 2007 U.S. Pat. No. 7,172,563, teaches using a microphone attached to a subject's body for picking up low frequency sounds from their feet, and an analyzer of the sounds transmitted through the subject's body while walking, from which gait characteristics of that specific subject can be determined. Hubbard, in 2002 U.S. Pat. No. 6,360,597, teaches the use of force-sensing sensors installed in a shoe insert worn by a subject, from which sensor electrical output data are analyzed for analysis of gait of a walking subject. Haselhurst, in 2007 U.S. Pat. No. 7,191,644, teaches the use of a pressure sensor and personal annunciator system installed in a shoe insole worn by a subject having difficulty walking, with which the system can tell the subject when the foot is contacting the floor, as a gait assistive device. Au, in 1989 U.S. Pat. No. 4,813,436, teaches the use of pressure sensors installed in the shoes or in shoe inserts worn by a subject, for measuring the subject's gait while walking, plus the use of video signals from two video cameras recording the motion of the subject who is wearing strategically placed visible markers such as on knees, elbows, and hips such that these data, along with the gait measurements, are presented to a practitioner to judge the subject's walking gait and, by overlaying these data on the video and gait of a "normal" subject, allows comparisons to be made.

The problem with all of the above methods is that they are invasive to the subject, are conducted in artificial testing environments, and that they present only data which subsequently require a skilled practitioner to interpret these data and draw conclusions as to the mobility of the subject, and in some cases to estimate the subject's risk of falling. To obtain an objective assessment, current fall risk testing systems and methods often use a 0-1 or 0-1-2 number scoring scale on each of 10 to 20 motion movements of a subject as assessed by an observer. These scores are totalled for a sum total number that describes an average risk of falling wherein a higher score indicates a lower risk of falling. For example, if in 20 movements, say, a subject scores 2 on each of 19 movements and 0 on one for a total score of 38, this result would normally be considered a low probability of falling.

Where the subject is an aged person or persons living in a senior's residence, home, long-term care or hospital environment the risk of falling is high. It is well known that these subjects are highly vulnerable to falling and that such falls often are devastating to the subject, their families and the providers of accommodations and care for them. The known techniques for assessing such risks do not lend themselves to such an environment where a large population has to be monitored on a continuous basis.

It is therefore an object of the present invention to provide a system, method and apparatus in which the above disadvantages are obviated or mitigated.

SUMMARY OF THE INVENTION

In general terms, the present invention provides A system for assessing the mobility of a subject, said system comprising a motion sensor to observe movement of a subject and generate a data stream representative of such movement, a comparator to detect abnormalities in such motion and compare said abnormalities to at least one known norm and an allocator operable upon an said comparator to indicate whether said output is within said known norm.

In a further aspect, the invention provides a method of assessing mobility of a subject comprising the steps of recording motion of said subject, analyzing said subject for abnormalities of such movement, comparing said abnormalities to known norms and indicating whether said abnormalities is within a known norm.

BRIEF DESCRIPTION OF THE DRAWINGS

Embodiments of the invention will now be described by way of example only with reference to the accompanying drawings in which:

FIG. 4 is a schematic representation of deviation from "normal" movement by a subject.

FIG. 5 is a schematic representation of a further deviation from "normal" movement by a subject.

FIG. 7 is a block diagram of the computer decision-tree structure for assessment of the risk of falling of a subject for a Sit-Stand-Turn-Sit movement.

FIG. 8 is a block diagram of the computer decision-tree structure for assessment of the risk of falling of a subject for a Walk-Slow-Negotiate-Walk-Fast movement.

FIG. 9 shows the equations for computation of the Stagger Condition (S) and for the Stagger Coefficient (ΔS).

FIG. 10 is a block diagram of the computer decision architecture for assessment of the risk of falling of a subject.

FIG. 11 is a block diagram of the personal assessor decision architecture with computer assistance for assessment of the risk of falling of a subject.

FIG. 12 is a schematic representation of stereoscopic 3-D observation of a subject in this example arising from a chair.

FIG. 13 is a block diagram of the logic decision architecture for the basic mobility assessment segment of the expert system.

FIG. 14 is a block diagram of the logic decision architecture for the advanced mobility assessment segment of the expert system.

DETAILED DESCRIPTION OF THE INVENTION

Figure 1:
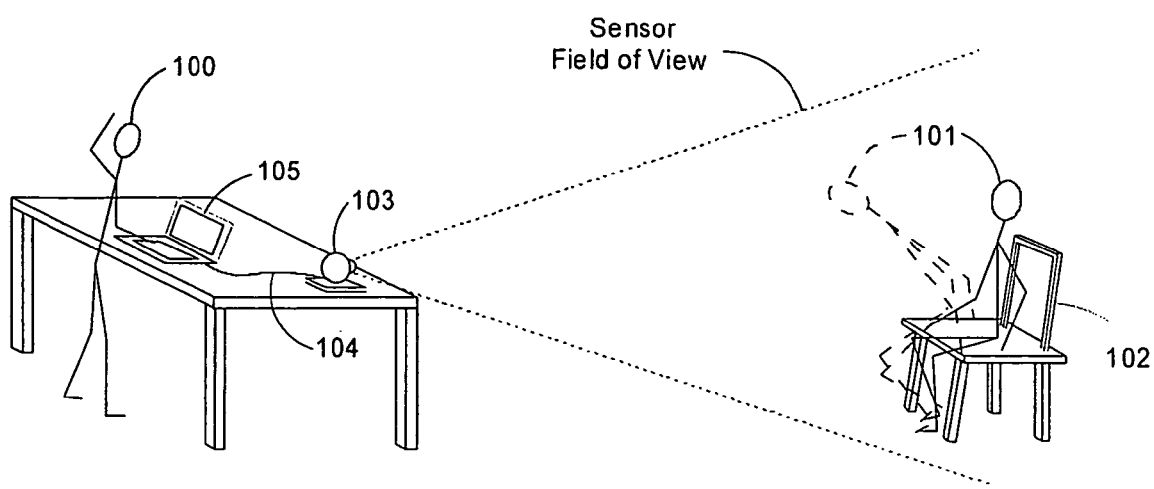
FIG. 1 is a representation of a 2-D assessment of a subject.

Prior to describing the system and its function in assessing risks, a number of the typical assessment environments will be described to provide context to the operation of the system. Referring therefore to FIG. 1, a motion assessment system is used within a typical professional office environment for observing and video-recording the movements of a subject, (101). The system includes a computer 105 that implements an expert system including a fuzzy logic neural networks decision engine to analyze video data obtained from a motion sensor (103). The motion sensor 103 may be a camera operating in the visible, infrared, ultraviolet spectrum, an acoustic image capturing device or location sensors such as GPS positioning devices or RF motion/location devices that generate information from which the movement of the subject may be determined. Multiple sensing devices may be used to obtain data of different parts of the subject, e.g. front, back, feet, hands, and the streams combined for analysis. For convenience they will be collectively referred to as a camera.

The data stream generated by camera 103 is subjected to algorithms and tests to enable the expert system to determine if the movement that has been observed is an abnormal condition, that is, one that departs from an expected or desired motion and commonly referred to as a stagger condition. The system utilises that information to assess a particular condition, such as a risk of falling. In FIG. 1, a subject (101, solid lines) sitting in a chair (102) is observed by a camera (103), connected via wire (104) to the computer (105) being operated by a test facilitator (100). The facilitator 100 may select from a range of standardized tests. The test conducted requires the subject to arise from the chair. The camera (103) detects the motion of the subject (101) and transfers the data representing the motion to the computer 105 for further processing.

As an example, say the subject takes two attempts to rise from the chair (101, dotted lines). The camera (103) captures the movement of the subject (101) in a time dependant manner and transfers the date to the computer (105). The expert system embedded in the computer (105) operates on and analyzes the data from the camera (103) and may prompt an observer to provide instructions to the subject or further inputs. The analysis can be done in real time during the live observation process or operating off-line analyzing the recorded video data following the observations.

As will be described more fully below, the expert system utilises a stagger algorithm to detect abnormal movement and applies this information and additional input to provide the criteria required to apply obtain standardized test criteria, e.g. the Tinetti test parameters. In the example provided, the two attempts to rise is recognized as a stagger condition and indicates that the subject has a significant risk of falling for that movement.

Figure 2:
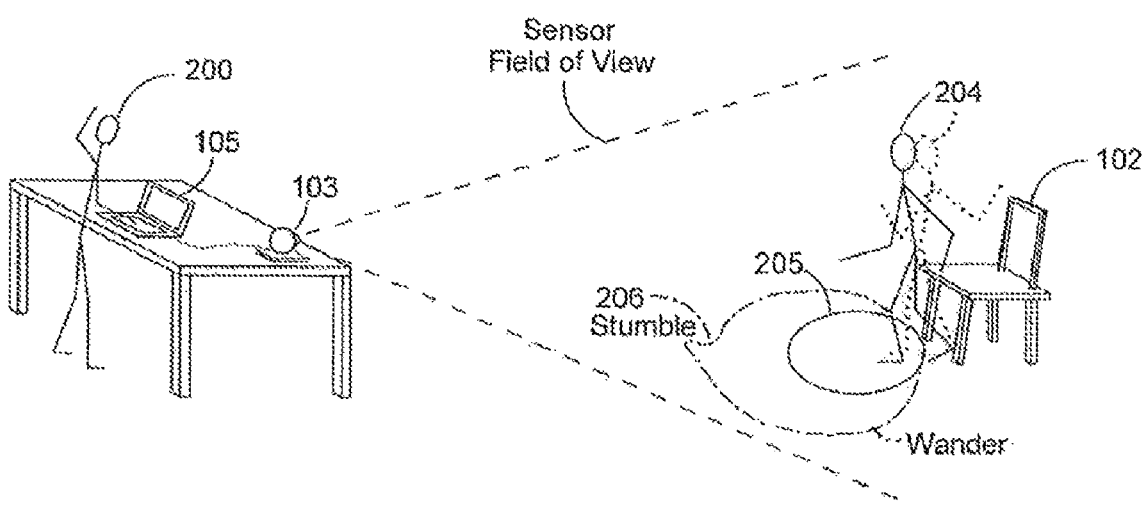
FIG. 2 is a schematic representation of a further assessment of the subject.

FIG. 2 shows a typical functional test assessment process and decision computations for a subject (201) to complete actions to rise from a chair (102), stand still, then turn around 360 degrees. The test facilitator (200) asks the subject, once the subject has risen from sitting in a chair (102), to stand still for assessing steadiness without wobbling or swaying, The computer (105) and the camera (103) capture the video data to record the movement indicated at 204, where solid lines stick-person subject and dotted lines stick-person subject indicate change of position over time to indicate that the subject is wobbling. In this test example, the expert system, processing in real time or offline, may recognize the wobble or swaying as being a stagger condition. These inputs are provided to the selected established test procedures and risk scoring, and, depending on the cumulative results, the expert system may decide the subject has a significant risk of falling for that movement (204). The expert system also scores the level of mobility of the subject's actions while standing (204), and wobbling, swaying or stumbling is detected, recorded and scored.

Continuing with this example, the facilitator then asks the subject to turn 360 degrees along the path 205, for which the solid line indicates the expected circular track for normal turning. The expert system observes the actual movement (206) indicated by the dotted line and analyses the data stream from camera 103 to recognize the wandering and stumbling as being a stagger condition. This is input in to established test procedures and risk scoring to determine if that the subject has a significant risk of falling for that movement.

Figure 3:
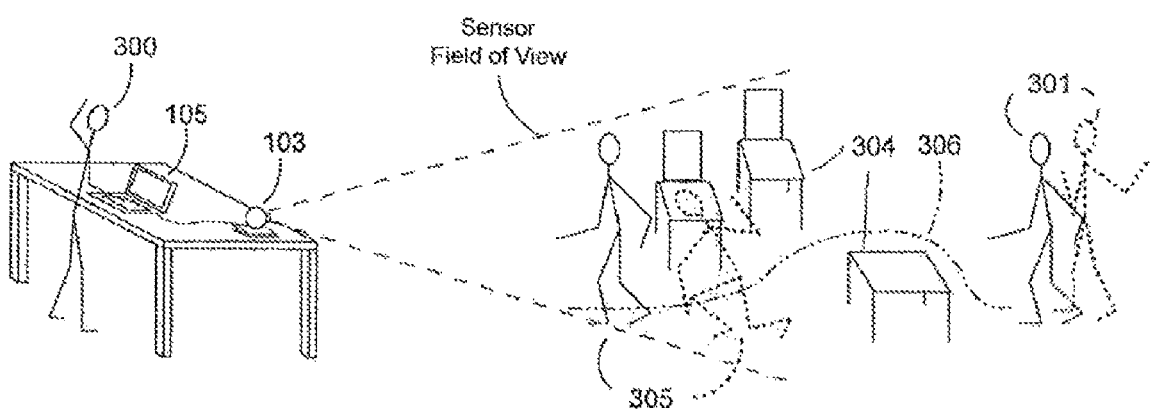
FIG. 3 is a schematic representation of a further functional test assessment process.

FIG. 3 shows a typical functional test assessment process and decision computations for a subject to complete actions from being in a standing position to then walk slowly forward while negotiating obstacles as a test of agility, vision, and mobility related to the risk of falling. The test facilitator (300) prompted to ask the subject 301, once the subject is standing still to walk forward, while the actions are captured with the computer (105) and the camera 103. The solid lines stick-person (301) subject and dotted lines stick-person subject indicate the subject is hesitating to start walking and may indicate possible cognitive problems or fear related to risk of falling. As the subject negotiates obstacles (304) any bumping or stumbling near them could indicate vision or agility problems related to a risk of falling. Then in walking out from where the obstacles were arranged, the departure from the path 305 of the solid lines stick-person subject and dotted lines stick-person subject indicate that the subject is staggering and recovers to continue walking.

The expert system evaluates the movement to detect stagger conditions, prompts for further input as needed according to the selected standardized test and determines whether the subject has a significant risk of falling for that movement. Similarly when test facilitator (300) is prompted to ask the subject to retrace the path (306) back to the starting position but at a slightly faster pace, the corresponding observations and decisions can be made, as well as timing the difference between slow and fast walking, allowing the expert system to make further decisions on the mobility of the subject and risk of falling.

There are many actions that can be used to observe and assess the mobility, occurrence of stagger conditions and risk of falling for a subject being assessed. FIG. 4 illustrates examples of two movements of a subject which would normally be detected by a stagger algorithm to deviate from expected "Personal" or "Standard" movement. "Personal" means movement that has been previously observed and recorded in databases for this subject and is accepted as a base level of mobility for this subject. "Standard" means movement that has been observed and recorded in databases of typical movements for subjects of similar age, sex, health, and mobility and is accepted as a base level of mobility for any similar subject.

In the stagger back example in FIG. 4, the subject in attempting to step forward (solid line stick figure), actually staggers backward (dashed line stick figure) in which the major motions of the subject's back and right arm would be detected by the stagger algorithm to deviate from expected for either the "Personal" or "Standard" movement. In the stagger forward example, the subject in attempting to step forward (solid line stick figure), actually staggers forward (dashed line stick figure) in which the major motions of the subject's back and right arm and left leg would be detected by the stagger algorithm to deviate from expected for either the "Normal" or "Standard" movement.

FIG. 5 illustrates movements of a subject's feet in which the subject's walking path wanders from a "Personal" or "Standard" path for the subject's feet indicated by a Deviation Right 1 and a Deviation Left 2 which would be detected by the stagger algorithm to deviate from expected for either the "Personal" or "Standard" movement. Further, FIG. 5 illustrates movements of a subject's feet which wander from expected "Personal" or "Standard" foot spacing where the subject's left to right Wander-1 spacing is larger than expected and right to left Wander-2 spacing is shorter than expected. The unexpected movements would be detected by the stagger algorithm to deviate from expected for either the "Personal" or "Standard" movement.

The above examples relate to an assessment performed in a controlled environment by a medical practitioner. The expert system may also be used in a normal non clinical environment as a continuous, non-invasive risk assessment tool.

Figure 6:
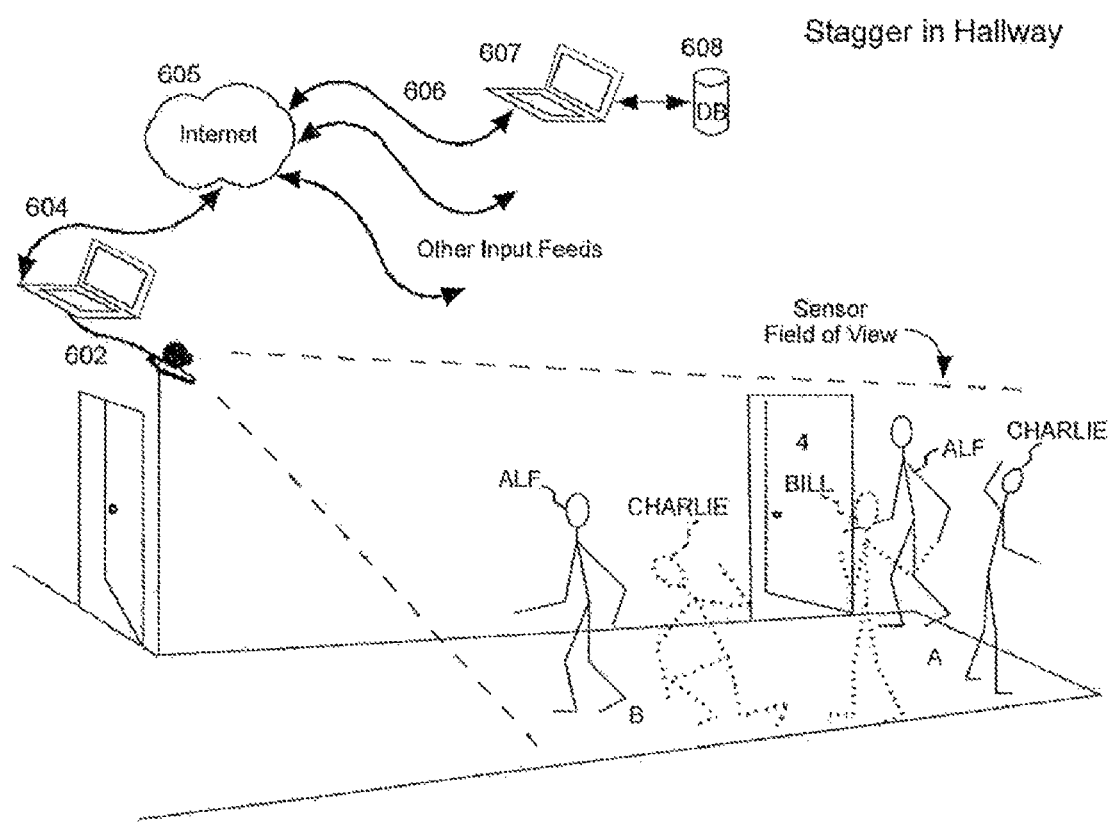
FIG. 6 is a schematic representation of "Normal" movement by two subjects and deviation from "Normal" by one subject in a hallway environment.

In a further example, shown in FIG. 6 a camera (103) is installed in a hallway and connected either wirelessly or through a cable (104) to a computer 105 implementing an expert system (603). That system may be located at the facility in which the observations are being conducted or may be connected through a network (604), such as the internet (605), to a remote facility (607) including databases (608). As shown in FIG. 6, illustrated are two subjects (Alf and Bob) walking to the left and one subject (Charlie) walking to the right in a hallway environment. In this example, say, Charlie waves to Alf and Bob and as Alf and Bob walk on further to the left, Bob attempts to wave back to Charlie but in so doing unexpectedly staggers. This is a non-clinical, everyday environment in which the system monitors the subject movement. Unexpected movements of Bob are detected by the stagger algorithm to deviate from expected for either the "Personal" or "Standard" movement. The system can then alert the relevant parties of the potential risk. This provides the capability of remote monitoring of a number of locations in both a real-time and recorded basis on a continuous basis with recognition of potential risks. The central monitoring can therefore service a number of facilities and provide individual identification for future assessment or remedial action.

In each of the above examples, the assessment of a subject is performed using an expert system that implements a stagger algorithm to determine appropriate action. The analysis of the data performed by the expert system will vary according to the specific applications and the environment in which it operates. In each case however, the stagger algorithm is used to assess the movement of the patient and to perform an assessment. That assessment may be assisted by reference to previous assessments where available and recommendations for mitigation and ongoing care may be generated by the expert system accessing a database of available options.

The implementation of the expert system can be considered as having two main linked components a basic mobility assessment system 1300, as illustrated schematically in FIG. 13, and an advanced mobility assessment system 1400, as schematically illustrated in FIG. 14. The basic system 1300 permits an operator to control part or all of the assessment process and to input assessments of the mobility of the subject being assessed. The advanced system 1400 contains the algorithms and computer facility fuzzy logic neural networks decision computations with which the expert system decides the assessment outcomes and recommendations according to established parameters, the action assessment total score number, and the differential comparison of current assessment to previous assessments, and generates reports of remedial actions, possible aids and healthcare procedures to the caregivers of the subject.

As illustrated in FIG. 13, to perform an assessment, an input from the operator, indicated at 1313 starts the camera 1301 to generate a video stream and a clock stream, 1302. The operator can select from a menu the features to be activated and the mode of operation. The data stream is supplied to database collection (1303), and provides for output of that data stream to the advanced system (1304) for the computerized algorithm assessment decision computations. A further operator input control (1314), permits assessment personnel to respond to prompts and assess (1305) the mobility of the subject, either from the real-time video data, or from previously captured data stored in video databases (1303). The assessment at step 1305 is performed by presenting prompts to the operator at 1314 which correspond to the inputs required for the expert system to apply the criteria to be scored in the standardized test that is applied. The aggregate scores are compiled by the scoring mobility engine 1316 and returned to the assessment database. The assessment is stored in a database (1306) and is linked to the corresponding video record in the database 1303. The data in the video database (1303) and results of the assessment in the assessment database (1306) can be presented and displayed and if desired the system can permit reassessment (1307) either by operator input control (1315) or automatically by the system.

Assessments derived from the advanced system algorithms (1308) are also integrated into the databases and display functions of the basic system (1307) if the operator (1315) has chosen to activate those functions. Additionally, the operator (1313) can decide and instruct the basic system which of the basic system assessments and the advanced system assessments are to be operating and storing data and assessments. The operator (1315) can instruct the basic system to display the data as raw video or, as discussed below as processed edge detected skeleton outline of the subject and to display these data and the resulting assessments of the mobility of the subject in a number of fashions. Typical modes of display include side-by-side video (1309) that depict the subject at different times, such as before and after treatment for the subject's physical or mental condition or disease; history of the subject's assessments over time (1310); details of any assessment and its components (1311); and any recommendations, treatments or aids (1312) that have been decided upon during the assessment process in either the basic system, such as by the operator (1315), or by the advanced system (1308). These displays can be video, numerical, charted, raw data, processed data, text, and audible, whether in electronic or non-electronic form and are generated by querying the data in the video database 1303 and assessment database 1306.

As illustrated in FIG. 14, the advanced system 1400 receives from the output 1304 of the basic system 1300 a video data stream (1401). The advanced system weight-averages and clusters the pixels (1402) in each video frame into groups, typically groups of 4 pixels by 4 pixels resulting in 19,200 such groups for each 640 by 480 pixel frame of video. Using known video processing techniques, the advanced system then detects the movement of each group from frame to frame by vector analysis (1403) and based on the movement detects the edge of the subject by differentiating between those groups that are moving and those that are stationary on a frame to frame basis.

Alternatively, a skeleton outline may be obtained by determining whether a given pixel with given color components M in image frame m moves/or is displaced by 3 or more pixel spaces in any direction for this pixel in its location in the next image frame, n. If so then this pixel in frame n is identified as moved and assigned new color components, say green. If pixel m in frame M moved less than 3 spaces at its new location in frame n, then this pixel is identified as not moved and assigned new color components, say black. By computing the movement of all pixels from frame m to their locations in frame n and coloring green all those that move 3 or more spaces, and coloring black all those that move less than 3 spaces, a "ghost-like", or skeleton motion-rendition of the subject's movements wherein all movement of the subject can be seen but details of the subject's face and identity are nearly impossible to recognize. The skeleton images of the subject are far clearer, more detailed and easier to follow than a simple edge detection technique described immediately above. However, in each case whether the edge detection or the skeleton techniques are used, the resulting image of the subjects movements protects the subject's privacy while the mobility fall risk assessment is unimpeded.

The video image processed at 1404 is stored in a database (1405). The motion is analysed at 1406 by a fuzzy logic decision engine that applies of a stagger algorithm to the observed motion to determine a stagger condition S. A suitable stagger algorithm is shown as Equation 1 in FIG. 9 which represents a linear combination for a given observation period t of the distance travelled, the number of steps, the degree of wobble, the wander and the departure from the circular path of the a 360 degree turn. Depending on the test being performed, the inputs may vary and the inputs may be fuzzified to reflect the interdependency of parameters. It is preferred that the stagger detection algorithms utilized are those of patent applications USPTO Ser. No. 11/011,973, and USPTO Ser. No. 11/520,705, the contents of which are incorporated herein by reference. By using such techniques, it is possible to obtain an indication that a stagger condition exists from analyzing the movements of a subject. Each of these evaluations may be made from the video data of the motion by comparing the average deviation of a set of pixels representing the body, e.g. the average location of the centreline of the subject, to the normal path. The results are then combined to obtain the stagger condition S. Of course the stagger algorithm will vary depending upon the assessment being performed but in general provides a cumulative indication of deviation of movement from an expected path.

Depending on the test being performed and the condition being monitored, prior results derived from prior assessments are loaded into databases 1408 and 1409 for comparison. If the assessment is against a prior assessment of the subject, i.e. a personal assessment, then data regarding the subject is loaded in to the databases. If however the assessment is against a known condition or a particular class of subjects, i.e. a standard assessment, data relating to that is loaded in to databases 1408, 1409. The results in data bases 1408, 1409 are prior characterisations of movement associated with the assessment as either "not normal" 1408 or "normal" 1409, and a comparison of the stagger condition S with those results enables the advanced system 1400 to decide if the motion of the subject is normal.

If there are no current data available with which the advanced system can make this decision, the operator (1407) can input this decision. In addition, by using this operator input, the advanced system can be trained to recognize and build databases of mean motions for either not-normal (1408) or normal (1409) motion of subjects for specific conditions or illnesses. Each database categorizes the motions observed to specific diseases, physical condition, mental condition, treatments, and the progress of any phases of these conditions, and therefore establishes "mean normal" and "mean not normal" values for that condition. The mean can be determined for both "normal" movements and for "not normal" movements and these can be determined from assessments of many subjects thus deriving a general mean which can be arranged by age, sex, condition, illness, disease and the stages of same. The mean can also be determined for both "normal" movements and for "not normal" movements from assessments of the subject thus deriving stages of the condition, illness, disease and stages of same specific to the subject.

By varying the stagger algorithm and the databases 1408, 1409, the stages of development of any such condition, illness or disease can be assessed. The databases 1408, 1409 are populated by observing many subjects at given stages and assembling a mean "not normal" database with realistic representations of that stage of the condition, illness, or disease. These mean databases that are "trained" to recognize these categories can pass this training to a mobility condition database (1414) and a condition treatment database (1416).

The databases 1414 and 1416 are accessed through a deviation function (1412), that implements a further stagger algorithm to determine a stagger coefficient, $\Delta S$, as shown in Equation 2 of FIG. 9. The stagger coefficient is indicative of the deviation of the results either from a previous assessment of the subject or the mean or norm for assessments of similar subjects. The output of the deviation function is supplied at 1417 to the basic system as a factor to be included in the assessment. It is also supplied to a classification function (1413), and a recommendation function (1415) components of the advanced system 1400 for further evaluation.

With sufficient mean data in the databases (1408 and 1409) the advanced system can decide, based on a comparison with the mean data, whether the motion is normal (1410); or the motion is not-normal (1411) and can store the skeleton outline data of the subject accordingly. If appropriate, the operator (1407) can override the advanced system to input the decision that the subject is to be assessed by the system as either: normal and data stored (1410); or as not-normal and data stored (1411).

Having access to all the databases of the Mean Not-Normal (1408), of the Mean Normal (1409), of the Subject Not-Normal (1411) and of the Subject Normal (1410), the deviation function (1412) can analyze the motions of the subject and can detect and assess the deviations from normal or from not-normal for the subject and provide (1417) these assessments to the basic system for database storage and display. The advanced system can then use these deviation measurements (1412) to classify (1413) the stage of the subject's mobility for the subject's conditions, illnesses, diseases, treatments. By accessing the mobility condition database (1414) a comparison with known classifications of mobility may be made, together with an assessment of the phase of the subjects illnesses or diseases. Assessment of mobility is an indicator in a number of diseases such as Parkinson's or Multiple Sclerosis MS and to conditions such as, stroke, or pain. A comparison with the data in the data base 1414 for records relating to the same conditions provides an evaluation of the subjects condition which is provided (1417) to the basic system for database storage and display. The advanced system 1400 can then use these classifications (1413) to query the condition treatment database (1416) and obtain a recommendation of treatments, aids, actions for these diseases and conditions. The condition treatment database 1416 contains records of the specific treatments, aids and actions and provides (1417) these assessments to the basic system for database storage and display.

Comparison of the assessment of the mobility of the subject to such mean "not normal" databases can provide a determination of the stage at which the subject's current condition, illness, or disease exists and which permits the expert system to access its databases for recommendation of treatments, aids or programs that might assist the subject to maintain or improve mobility and reduce risk of falling. Additionally, the expert system can compare past assessments made before a specific treatment has been administered to the subject, with an assessment or assessments after the treatment has been administered from which the expert system can assess the change in mobility and change in risk of falling. The effectiveness of such treatment can then be determined, be it medication, physiotherapy, diet, psychological, surgery, healthy activity or simply the subject's personnel healing process.

It will be seen therefore that the incorporation of the stagger algorithms in to the expert system querying the records of prior assessments provides enhance inputs to an individual assessment and indicates suitable treatments and activities for the subject.

As a general overview of the operation of the advanced system 1400, the data stream representing the motion of the subject is processed and provided as an input to a fuzzy logic decision engine. The operator is able to select the type of test to be performed and the category of conditions that are being assessed. For a general assessment, for example of an elderly person, the mobility condition database is queried to provide a "mean not normal" condition for a person of the subjects age group and sex and similarly to provide a "mean normal" condition. The records queried in the mobility condition database are limited to those for a comparable test, e.g. the sit and stand test, and comparable condition, e.g. age and sex. Similarly, if a specific condition is being assessed, e.g. whether MS is indicated, the mean normal and mean not normal are queried from the mobility condition database for that set of parameters.

The data stream representing the motion is analyzed using the stagger algorithm and the results compared with the mean normal and mean not normal databases. The abnormalities determined by the stagger algorithm indicate whether or not the results are comparable with the known norm found in either the databases and the results are allocated to either the "mean not normal" or "normal" databases.

Thereafter, the results of the comparison is provided to the measure deviation from normal function which compares the current assessment to previous assessments of the same subject. The result is also passed to the classify stage where it is compared with sets of records representing different conditions such as Parkinson's, MS, stroke or pain. If, in the general example, no abnormality is detected during the initial assessment against the general population, then it would be expected that no identification of one of those conditions would occur. If however, an abnormality has been detected, then the comparison against each of the conditions may detect a possibility that the subject has such a condition.

In that situation, the mean normal and mean not normal databases are reloaded with conditions pertinent to that condition and a further comparison is made. At each iteration, a refined assessment for that particular condition is obtained and a comparison with the mean normal for each condition and phase of that condition provides an accurate assessment of the subject.

The operator may select successive evaluations based on the results of the previous evaluation or may initiate a sequence of such evaluations so that the data stream is analyzed for abnormalities and subjected successively to different comparative tests against the mobility condition database records until a full assessment of potential conditions is obtained.

By way of example, the logic applied to a formal assessment under controlled conditions is illustrated in FIG. 7. FIG. 7 illustrates the sequence of events for the "arising from a chair" and "turning 360 degrees" test strategy shown schematically in FIG. 2. The assessor starts the assessment (LD101) and is prompted to ask the subject to rise (LD102). The data captured by the motion sensor is processed by the stagger algorithm to determine if there are deviations from normal (LD105). If no deviations are determined, the subject is assumed to have arisen normally and an appropriate score is accorded in the subjects recorded. If the subject arises normally, the assessor is prompted at LD104 to ask the subject to turn 360°, and that motion is assessed by the stagger algorithm and scored accordingly. If a deviation is noted, the expert system accords an appropriate score which is recorded in the subject's record. The expert system then prompts the operator for further information and to perform further actions as the test proceeds. The relevant information is recorded at each stage to provide a cumulative score on the selected test. This is the functioning of the Basic System. During or upon completion of the test, the advanced system 1400 is invoked to determine through implementing its decision engine if the observed movement has been interpreted as a stagger condition to which the system may assess a risk of falling. This data is provided to the basic system 1300 for inclusion in the cumulative score. The system scores the actions of the subject's movements, totals all the scores and assesses the mobility and risk of falling of the subject (LD108), decides if stagger conditions are detected, and computes the total risk of falling as determined by the stagger conditions and stagger coefficient (LD109). The decision is subject to predetermined ranking of scoring for example, give a maximum score of say, 100, the risk can be defined as: low for scores above 70; moderate for scores from 30 to 69; and high for scores from 0 to 29. During the training of the algorithms for "normal" and "not normal" these scoring rankings can be revised, developed and expanded as required.

The use of the computer with an expert system capability to assess the mobility and risk of falling of subjects enhances the analysis of a subject. The expert system, by recording sequential time during the observations of subjects, can measure time intervals for subject's movements down to fractions of a second, say, one thousands of a second and can measure and analyze the subjects movements to such intervals. The time taken by the subject to make movements and the minute analyses of these movements can be important data the expert system uses in its decision making processes. Further, even down to the image to image and pixel to pixel levels, the expert system can compare these timed movements from the subject's present assessment, to the timed movements of earlier assessments for the subject from which to detect change, deterioration, improvement in the assessment of risk of falling. The expert system can also make comparisons to "Personal" or "Normal" movements stored in its databases as part of the assessment.

Further, the movements of subjects being observed and analyzed by the expert system can be conducted in many different environments such as testing environments like clinics, hospitals, practitioner's offices; or natural everyday surroundings like hallways, residences, apartments, walkways, streets, stores, malls; or confined spaces environments like industrial, commercial, experimental, and manufacturing.

The observation and assessment of the risk of falling or condition of staggering or condition of falling are applications of the expert system. In some cases making these observations can influence or imply to the subject the need to perform and to do well on the assessment which can occur in a clinical environment. However, it is clear that these observations can be arranged to be unobtrusive, passive applications such as in natural everyday environments which can go unnoticed, and thus the observations do not affect the movements or performance of the subject.

In the above discussion of Logic Diagram 1, FIG. 7, "arising from a chair" and "turning 360 degrees" mobility risk of falling assessment examples, the expert system can use the advanced system 1400 to also compare the present assessment to previous assessments (LD110) and compute the differential times taken for each action using the sequential time clock (LD101). Comparing the times (LD111) taken for each action in a previous assessment to the present assessment, the expert system can compute the differential time coefficients for each stagger condition or action from which to assess if the condition or action has remained the same, improved or deteriorated. The system can also compute the stagger condition (Equation 1) from which a stagger coefficient (Equation 2), as illustrated in FIG. 9, can be used to further define the stagger condition and changes in that condition with time. This computation is in addition to the computations and decisions of mobility described in 1400 and can further refine the assessment of mobility, and stage of the subjects condition, illness, disease, treatment effectiveness, and progress in same.

From the above computer facility fuzzy logic neural networks decision computations, the expert system decides (DL112) the assessment outcomes and recommendations according to established parameters, action assessment total score number, and differential comparison of current assessment to previous assessments, and reports (DL113) remedial actions, possible aids and healthcare procedures for the caregivers of the subject. These recommendations could be, but are not limited to, assigning a repeat of the assessment for confirmation, assigning a follow up assessment upon confirmation of a risk of falling, and reporting electronically or by hardcopy output to the caregivers or the subject's family or the subject's professional advisors.

FIG. 8, Logic Diagram 2 (LD201, Walk Slow-Negotiate-Walk Fast Mobility) illustrates another test of the subject's mobility and risk of falling similar to that of Logic Diagram 1. In the Walk Slow-Negotiate-Walk Fast Mobility, the assessor starts the assessment (DL201) and the subject is asked to walk slowly (LD202), perhaps showing hesitation (LD203) or needing aids (LD204) to walk normally (LD205) without body sway (LD206), to negotiate obstacles (LD207) and to retrace this path at a faster pace. The expert system, observing and video-recording, and analyzing (LD203-207), while operating in real time during the live observation process or operating off-line analyzing the recorded video following the observations video-recording the movement, for which the system employs computer facility fuzzy logic neural networks decision computations in a computer to analyze the video data of those movements according to specific algorithms and tests, scores the actions of the subject's movements, assesses the mobility of the subject, and computes the total risk of falling determined by this assessment (LD208). The system further determines if the observed movement has been interpreted as a stagger condition to which the system may assess a risk of falling, and decides if stagger conditions are detected, and computes the total risk of falling as determined by the stagger conditions and stagger coefficient (LD209).

In the above "Walk Slow-Negotiate-Walk Fast" Mobility risk of falling assessment examples, the expert system can also compare the present assessment to previous assessments (LD210) and compute the differential times taken for each action using the sequential time clock (LD201). Comparing the times (LD211) taken for each action in a previous assessment to the present assessment, the expert system can compute the differential time coefficients for each stagger condition or action from which to assess if the condition or action has remained the same, improved or deteriorated. The system can also compute the stagger condition (Equation 1) from which a stagger coefficient (Equation 2), as represented in FIG. 9, can be used to further define the stagger condition and changes in that condition with time. This computation is in addition to the computations an decisions of mobility described in 1400 and can further refine the assessment of mobility, and stage of the subjects condition, illness, disease, treatment effectiveness, and progress in same.

From the above computer facility fuzzy logic neural networks decision computations, the expert system decides (DL212) the assessment outcomes and recommendations according to established parameters, action assessment total score number, and differential comparison of current assessment to previous assessments, and reports (DL213) remedial actions, possible aids and healthcare procedures to the caregivers of the subject.

The advanced system 1400 includes the computation of the stagger condition S and the stagger coefficient as components utilized in the assessment of the risk of falling. FIG. 9 illustrates the format of these computations for Stagger Condition (Equation 1) and the Stagger Coefficient (Equation 2) as performed by the computer as part of the continued observation of the data. The process architecture for the risk of falling assessment computations by the expert system are computer derived decisions made from video data of the subject as illustrated in the block diagram of FIG. 10.

In FIG. 10, the process architecture for the expert system assessment of the risk of falling is illustrated in block diagram format. The process begins as an operator initializes the expert system which begins observations and recordings of the motions of a subject, capturing images at 10-30 frames per second with timing markings of $\frac{1}{1000}$ sec. The recordings can be encrypted for security and privacy. The expert system can compare the observations of the subject's motions, in real-time or after recording them, to earlier "Personal" observations of the movement of the subject or to "Standard" observations of similar subjects as stored in the systems databases. Comparisons of the present observations to the "Personal" and "Standard" base-line movement data have been explained earlier, and are used by the expert system running the stagger algorithms to determine the Risk of Falling Assessment. Using the timing markings the system can compute the deviations from "Personal" or "Standard" by image to image and by pixel to pixel to determine a stagger conditions and the stagger coefficients related to the risk of falling. Thereafter, the results for that particular assessment may be compared to the databases to obtain the change for that subject from previous assessments and/or the status of that subject relative to norms in particular categories.

FIG. 10 illustrates that depending upon results of these factors determined by the expert system, the system then can, as explained with respect to FIG. 14, access databases and consider other information about the subject, such as but not limited to, use of drugs, health and condition, use of mobility aids, and previous data from caregivers and professionals, which together with the current assessment results, the expert system can determine actions to follow, recommendations and the completed current assessment. The expert system can then decide on scheduling of further assessments, such as but not limited to confirmation or regular assessments, and can access databases of recommendations related to the current assessment results with which the system can make decisions as to use of potential mobility aids, drug regimes, and programs, such as but not limited to, exercises or physiotherapy, and to report these results and recommendations to caregivers, professionals and health care groups as well as to other centralized data systems for recording and further analysis.

FIG. 11 illustrates the case where the capability of the expert system to present the "skeleton" imagery rather that the video data imagery has been chosen. In a further preferred embodiment of method and apparatus of the invention, a qualified personal assessor can make the decisions from live real-time or recorded playback utilizing computer assistance. In FIG. 11, a block diagram illustrates the process architecture for a human assessor, to determine the risk of falling by observing the movement of a subject being observed and recorded by the expert system as described earlier and shown in FIG. 10. In the FIG. 11 case, however, the Assessor is only being assisted by the expert system which can display the observations live or in playback and in video movements or the "skeleton" movements. The expert system can display for the assessor, lists of accepted movement criteria and permit the assessor to select and score the observed subject's movements, and the expert system can record these selections and scores. At this point the assessor can decide to use only these scores and to have the expert system compute total scores and determine the risk of falling according to the established criteria. The assessor can then determine what results and recommendation to make and to whom to report them for follow up actions.

Further however, once the assessor has completed the assessment of the movements of the subject, the Assessor can have the expert system proceed as earlier described for FIG. 10, to determine the variations, deviations, stagger conditions and coefficients, and combine these results with the assessors determination of the risk of falling, for the system to then compute and arrive at a new determination of the risk of falling. By combining the assessor's determinations and the expert system's determinations, the resulting assessment of risk of falling may be improved. The assessor can then have the expert system decide on what results and recommendations to make and to whom to report them for follow up actions as earlier discussed and illustrated in FIG. 10.

Additionally, the expert system could decide the risk of falling is sufficiently great to recommend installation of facility for a 24-hour video/motion monitoring/recording system in the subject's living quarters or where the subject is known to move about. Such a system could be arranged to erase the previous 24 hours of recording if the system has been notified by the subject's caregivers to do so. If saved, this recording could be used for further analysis of the occurrence of a stumble, stagger or fall and, could provide information for subsequent response of authorities. A more advanced installation of a facility could be recommended to include with the 24-hour system an additional computerized movement stagger analysis such as indicated herein, with which the facility could automatically detect a stagger condition which would tell the facility to retain part or all of the 24-hour video/motion monitoring/recording and to start a new 24-hour video/motion monitoring/recording. And yet a more advanced installation of a facility could be recommended to include, with the 24-hour system and additional computerized movement stagger analysis, a fall detection analysis capability. Such a more advanced facility could not only automatically detect a stagger but it could also detect a fall, with or without a preceding stagger, for which notification of the fall to the subject's caregivers could provide quicker response and assistance being given.

All three of the above facilities could utilize data encryption technology for protection of privacy, but with legal authority could be viewed to establish what movement occurred, where it occurred, and possibly why it occurred. This information, accompanied by the assessment results, could provide valuable assistance to improve the care given to the subject, improve the quality of life for the subject and provide important evidence in case of any legal, insurance, liability, or publicity actions that could arise from the mobility or lack of mobility of the subject.

Privacy can also be a requirement for the video recording used in the fall prevention and assessment methods and apparatus being revealed in this patent. Several different methods can be used to render the subject not recognizable in the assessment video recordings of the subject. Methods can include electronically altering the subject's facial features in the video recording, removing color components in the video recording, and electronically erasing the head of the subject in the video recording.

In a preferred embodiment of the apparatus and methods of this invention, the video processing of a skeleton image can transform the images of the subject in the video recording to become an outline of the subject with full retention of all movements of all of the subject's body including feet, legs, trunk, arms, hands and head while rendering the recording devoid of the information needed to identify the subject. In this way the subject's privacy can be maintained while the mobility fall risk assessment is unimpeded.

In an alternative embodiment images from multiple cameras may be used as shown schematically in FIG. 12 (camera A 103a and camera B 103b) sitting on a table (1211) or any other stand or facility. The cameras are separated by a distance (1210) and observe the subject with separate fields of view (camera A view 1208 and camera B view 1209) The video data from each of the cameras is connected via cables (1205) and (1206) to the controlling and data collecting computer facility 105 of the expert system as operated by the test facilitator (1200). The data is composed into a stereoscopic 3-dimentional (3-D) representation of the subject's movements using known image reconstruction techniques, and can transform the images of the subject in the video recording to become an outline of the subject with full retention of all movements of all of the subject's body including feet, legs, trunk, arms, hands and head while rendering the recording devoid of the information needed to identify the subject. In this way stereoscopic 3-D modeling of the subject's movement can provide more precise and more accurate determination the subject's movements and the subject's privacy can be maintained while the mobility and fall risk assessment is unimpeded.

Using the methods and systems described above to observe and video record the movements of subjects, using a wide variety of tests and algorithms employing computer facility fuzzy logic neural networks decision computations, it is possible to assess the risk of falling, and with appropriate detection facilities can detect falling. The results of these assessments and computations can be used by the expert system to recommend particular mobility aids such as use of canes, walkers and wheel chairs and implementation of remedial programs such as physiotherapy, exercise and strengthening routines, as well as healthcare programs, any or all of which can be preventative actions for the risk of falling as determined from these assessments. Reporting of these assessments and actions, whether electronically, such as computer to computer or e-mail, and digitally such as magnetic media such as CD's, DVD's and hard copy printed and graphic documentation, provided to the assessed subjects' caregivers, professional advisors, family members or the subjects, can be vital in informing them of the risk of falling, and planning for fall detection and response, with the intention of predicting and preventing falling. The reporting of these assessments isn't necessarily vital in discovering the risks of falling, though it is vital for preventing, predicting and planning to manage the risks of falling.

In experiments conducted to date to test and validate the assessment methods and apparatus it is was found that the methods and apparatus were well received, functional and highly accepted as providing valuable information. The linkage between current and previous assessments in evaluating the changes in mobility and risk of falling was also recognized. We also have been able to recognize the preventative aspects of following the assessments with stagger monitoring and fall detection facilities implemented in the seniors' residence.

The system described above has the capability to compare a subject's present assessments to their previous assessments whereby the expert system can detect and measure the changes in any of the actions and motions of the subject specifically tailored to the subject's individual conditions and health. The expert system not only has databases of information on what are considered normal movements and actions of persons depending on age, sex, health condition and drug use, but also has similar databases specific to the subject being assessed, and thus the expert system can also base-line calibrate its decision-making computations to what are considered normal movements and actions of the subject being assessed. Using the subject's base-line the expert system decision computations can determine if the present assessment is normal or if it indicates a stagger condition and possible risk of falling. If the system decides that a stagger condition exists, then the system can compare the present assessment to previous assessments for this subject to determine changes in the stagger conditions. Further, if video monitoring in areas where the subject moves about, such as but not limited to, in a residence, home, hospital, long-term care or natural environments are implemented as the earlier discussion noted, the expert system analyzing these correlated data can also permit the system to detect staggering and falling and changes in the subject's mobility in the subject's daily living environment from which the system can decide on and recommend more comprehensive preventative and remedial practices, health and well-being programs, mobility aids, and monitoring programs for fall prevention and improved quality of life activities for the subject.

In either real-time or post-recording, the expert system can be the decision-making facility which permits the actual operation of the system and assessment to be done by regular staff of the subject's residence without the need for highly qualified and expensive professional personnel. The expert system can also utilize its decision computations to review part or all of the assessments done for the subject so as to provide the history of the subject's mobility, staggering, risk of falling, and fall detection, from which the system can project fall prevention and remedial practices and recommendations based on the full history of the subject's mobility as stored in the system's databases and, if access is available to the expert system, by using data from databases of other systems.

The apparatus and methods described above can also allow authorized personnel, such as a professional physiotherapist, to review the data and the decisions made by the system, and the system can allow that personnel to score new data values for any and/or all mobility observations of an assessment thereby creating a new or updated assessment which can be recorded accordingly.

The expert system can also transmit the results and recommendations of the current as well as previous assessments via electronic, digital, analogue or hard copy media to the subject or the subject's caregivers, medical practitioners, family or legal representatives. Results so transmitted can allow others to review the assessments and data allowing them to provide second opinions and guidance for the subject. The expert system utilizing standard plotting methods can provide viewing of these assessments results over selectable time periods, including the entire time that assessments have been done for the subject, thereby allowing viewers improved ability to follow and understand the changes in the subject's mobility. This historical review of assessments can permit improved recommendations to be made by those others provided access such as, but not limited to, scheduling further assessments, ordering mobility aids, planning new activities and body-strengthening routines and implementing video monitoring activities, as fall risk, fall preventative and fall detection measures that could be implemented.

The expert system can also utilize its decision computations to review part or all of the assessments done for the subject so as to provide the history of the subject's mobility, staggering, risk of falling, and fall detection, and screen for the existence or potential existence of any of a number of diseases that reflect in the mobility of the subject such as: Multiple Sclerosis (MS), Parkinson's Disease (PD), Alzheimer's (ALZ), Dementia (DE), or Stroke (ST).

As noted above, the system may use 2-D video data or from three dimensional, 3-D video data. For many motions such as staggering or wondering in the walking path of subjects, 2-D video data may be adequate to analyze and assess the mobility of the subject. However, for some motions such as the quick motion of uncontrolled shaking of the hands or head of subjects, 3-D video data may be required for assessing the mobility of the subject.

From the above it will be clear the assessment methods and apparatus described could be applied to many environments other than seniors' residences such as, but not limited to, hospitals, private homes, hotels, commercial establishments, doctor's offices, clinics, drugstores, mobility-aids stores, and in the broad sense anywhere people are moving about. Also it will be clear to anyone versed in the healthcare field that many different algorithms, test parameters, action scoring methods and analyses can be implemented, including, but not limited to, stagger algorithms, time derivative analyses and mobility testing, such as those we reveal as incorporated into the computer facility fuzzy logic neural networks decision computations methods and apparatus with which we can assess the risk of falling, the preventative outcomes and recommendations to reduce falling and for improved quality of life for assessed subjects. Further, it will also be clear that the methods and apparatus, assessments and recommendations facilitated by the expert system can have application to any subject persons regardless of their age, health, sex, location or activity. Also, it will also be clear that the methods and apparatus, assessments and recommendations facilitated by the expert system can have application to assessment of and the progression of many diseases and the effects of treatments whether trials or long-term such as but not limited to drugs, physiotherapy, nutrition, exercise, and success or failure of those treatments, for those diseases such that applications are not limited to only those diseases disclosed herein.

In this example, the expert system analyses the data available to identify that a stagger condition exists in one or more movements in the current assessment and accesses a data base to compares this stagger condition to a previous assessment for this subject, stored in the database component of this system, to determine if this stagger condition was detected in a previous assessment. If the stagger condition did so exist, the computer system, using time derivative analysis, calculates the rate of change in the stagger condition between successive assessments for this subject. The computer facility, using a predetermined baseline matrix of outcomes, then determines if a critical stagger condition exists and, comparing to previous assessments, determines if a deterioration in the stagger condition has occurred, and if so occurring computes the rate of change of this deterioration.

What is claimed is:

1. A computer implemented system for assessing the mobility of a subject, said system comprising:
   a camera to record motion of said subject;
   a motion sensor to receive an output from said camera and determine movement of said subject, said motion sensor generating a data stream representative of such movement;
   a database;
   a first computer implemented assessment engine including a computer generated prompt to prompt an operator to provide data related to a test being performed by said subject,
   an input to permit an operator to provide additional data in response to said prompt for recordal with said data stream in a database;
   said system further including a second computer implemented assessment engine including a comparator to permit a comparison between motion represented by said data stream and representative movements recorded in said database to indicate whether said output is within said known norm, an allocator operable upon an indication of said comparator to allocate said motion to either a known norm or outside a known norm, and a deviation function to compare motion represented by said data stream with a representative movement and to detect abnormalities in such motion, and;
   an output to indicate to an operator a classification of the mobility of said subject.

2. A system according to claim 1 wherein said database is organized to provide a pair of subsets of said database, each of which provides a respective known norm derived from the contents of the database, said comparator comparing said abnormalities to said known norms provided by said subsets of said database.

3. A system according to claim 2 wherein said allocator is operable to add said abnormalities to one of said databases.

4. A system according to claim 3 wherein said comparator implements a stagger algorithm to detect abnormalities.

5. A system according to claim 4 wherein said comparator incorporates a fuzzy logic decision engine to implement said stagger algorithm.

6. A system according to claim 2 including a mobility condition database containing records of abnormalities of prior assessments to permit the said output to be compared to prior assessments.

7. A system according to claim 6 wherein records of said mobility condition database include categories of conditions to permit said output to be compared to selected conditions and a classification of said condition obtained.

8. A system according to claim 7 including treatment database to permit said classification to generate a treatment regime.

9. A method of assessing mobility of a subject using a computer implemented system having a camera to record motion of said subject; a motion sensor; a database; a first computer implemented assessment engine and a second computer implemented assessment engine, said method comprising the steps of:

recording motion of said subject with said camera, utilising said motion detector to determine movement of said subject from an output from said camera, utilising said first assessment engine to prompt an operator to provide data related to a test being performed by said subject, recording an input provided by said operator in response to said prompt with said data stream in said database;

utilising said second computer implemented assessment engine to:

perform a comparison between motion represented by said data stream and representative movements recorded in said database, determining whether said comparison is within a known norm, allocating said motion according to whether or not it is within a known norm, applying a deviation function to compare motion represented by said data stream with a representative movement and to detect abnormalities in such motion, and;

providing an output to indicate to an operator a classification of the mobility of said subject.

10. A method according to claim 9 wherein said abnormalities are detected using a stagger algorithm.

11. A method according to claim 10 including the step of generating said known norms from a database of prior assessment.

12. A method according to claim 11 including the step of comparing said abnormalities to prior records of said subject.

13. A method according to claim 11 wherein said abnormalities are compared to prior assessments of different conditions.

* * * * *